United States Patent [19]

Garretson

[11] Plant 4,801

[45] Jan. 19, 1982

[54] APPLE TREE

[75] Inventor: John W. Garretson, Yakima, Wash.

[73] Assignee: Carlton Nursery Company, Inc., Dayton, Oreg.

[21] Appl. No.: 99,091

[22] Filed: Nov. 30, 1979

[51] Int. Cl.[3] ..... A01H 5/03
[52] U.S. Cl. ..... Plt./35
[58] Field of Search ..... Plt./35

[56] References Cited

U.S. PATENT DOCUMENTS

| | | | |
|---|---|---|---|
| P.P. 1,822 | 3/1959 | Gilbert | Plt./35 |
| P.P. 2,433 | 8/1964 | Miller | Plt./35 |
| P.P. 3,485 | 2/1974 | Coke | Plt./35 |
| P.P. 3,974 | 11/1976 | Slusarenko | Plt./35 |
| P.P. 4,159 | 11/1977 | Silvers | Plt./35 |

*Primary Examiner*—Robert E. Bagwill
*Attorney, Agent, or Firm*—Harvey B. Jacobson

[57] ABSTRACT

An apple tree characterized by its compact, dwarf growing habit.

3 Drawing Figures

1

This discovery relates to a new and distinct variety of apple tree which was discovered by applicant in 1961 in the vicinity of Yakima, Wash. The new apple was found in applicant's orchard of Starking Delicious, and was first noticed because of its bright red, blush type fruit color. The original Starking Delicious possesses the characteristic Red Delicious striped coloring, while the new apple has coloring comparable to that of Starkrimson Spur.

Originating as a bud sport, this new apple could not be propagated for testing for a period of 3–4 years after its discovery. Great difficulty was encountered in forcing vegetative growth from buds on the short, spur branch on which the original fruit was borne. When adequate wood for grafting was finally produced, test plants were propagated.

Through succeeding propagations it was noted that the new apple possessed not only a fruit color different from that of its parent, but also exhibited an altered growth habit. The new tree is dwarf and more compact. The extent of the dwarfness is considerable, the new type growing to only about half the size of the well-known Starkrimson. Shortened internodes are present, as well as slightly thickened leaves, common to dwarf or compact spur types. Further propagations by grafting or budding have resulted in the transmission of these characteristics, indicating them to be genetic in nature.

The dwarfness of this new variety combined with its already well accepted fruit type make it a desirable tree. Having these characteristics, it should prove useful in both home plantings and some of the newer types of orchard systems.

The fruit produced on the new variety has an elongated and uniformly ribbed appearance with five distinct points and a round-conic shape. It has the rich distinct taste and flavor of the "Delicious" variety.

The food exhibits a very distinct early coloring factor and colors to a brilliant solid red color at maturity. Yield data taken in 1979 from 16 year old trees in a test block averaged 2,034 loose boxes per acre. These trees were growing at an orchard site near Parker, Wash.

A comparison of the subject new variety with other spur-type red delicious clones discloses that:

1. The new variety developed as a small branch which arose spontaneously from a fruiting spur and can be described as a true "Gene Mutation" which differs

2 from the parent tree upon which it was discovered; whereas other spur-type varieties listed herein which are commonly propagated and sold in the trade, developed as whole-tree sports.

2. All of the varieties listed for comparison are described as having a red early fruit-coloring character followed with bright-red over-all color formation at harvest time. The new discovery does not differ from this description and exhibits this same early-coloring character and over-all bright blush-red color formation at harvest.

3. Other spur-type Red Delicious clones which are compared to the new variety are listed below. Comparative differences relate to and emphasize particularly the ultra dwarfness of the new discovery. This, is the primary difference between it and other spur-type Red Delicious clones.

The following comparative descriptions which relate to growth characters are derived from observations and are also taken from nursery catalogue and U.S. plant patent descriptions.

a. Redspur Delicious (Gilbert Strain — U.S. Plant Pat. No. 1,822)
   This clone is described as a new variety of "semi-dwarf growth".
b. Sturdeespur Delicious (Miller Strain — U.S. Plant Pat. No. 2,433)
   This variety is described as possessing "a true semi-dwarf habit of growth".
c. Oregon Spur Red Delicious (Trumbull Strain — U.S. Plant Pat. No. 2,816)
   This clone is described as a "semi-spur type grower".
d. Rose Red Delicious (Coke Strain — U.S. Plant Pat. No. 3,485)
   This variety is listed as a "semi-dwarf spur-type tree" and is also described as a "natural semi-dwarf tree".
e. Redchief Red Delicious (Campbell Strain — U.S. Plant Pat. No. 3,578)
   This clone is listed as a "semi-dwarf spur-type tree".
f. Silverspur Red Delicious (Silvers Strain — U.S. Plant Pat. No. 4,159)
   This variety is listed as a "semi-dwarf tree".

All of these spur-type Red Delicious clones are listed and described as possessing a "semi-spur" or "semi-dwarf" type of growth character. Observations indicate that considerable size differences do exist between the semi-dwarf clones listed for comparison and that they exhibit a dwarfing factor in the range of 25–40 percent at tree maturity when compared to mature trees of standard non-spur type varieties. In comparison, the new variety exhibits a 50–55 percent dwarfing factor when compared to its non-spur type parent.

Its extreme dwarf growth habit allows growers to choose trees propagated on a number of clonal rootstocks which exhibit good root anchorage but are not now commonly used before they lack high dwarfing ability. The new variety, when propagated on such stocks allows for ultra-dwarf freestanding blocks of trees which need no additional tree support systems.

Continued observations of second and subsequent generations of trees propagated from the limb-sport over a 16 year testing period show that it is a new and distinct type of Red Delicious variety as particularly evidenced by its extreme ultra-dwarf character of growth and its very sub-compact natural tree size. These comparisons being made with all other Red Delicious varieties including all other so-called spur-type Red Delicious strains.

The accompanying photographs show a mature 16 year old tree (height 9 feet), and the fruit of the new variety with certain of the fruit shown in cross-section.

The following is a description of the new variety.

Tree

Branches: Straight to gently curved; dark reddish-brown; lenticels obvious, slightly raised, generally tan with white along lateral margins, moderate in number; generally smooth, with fine, white pubescence, at times less evident at and above nodes; internodes 25–30 mm.

Leaves: Foliage very abundant; buds of average size, obtuse, somewhat appressed to the stem; leaves ovate to lanceolate, apex acuminate, margins serrulate (some irregularly), approximately 50–75 mm long, 25–35 mm wide, medium to dark green above, lighter beneath, glabrous above, finely pubescent beneath. Petioles light to medium green, 15–25 mm in length. Stipulate, stipules linear to long lanceolate.

Flowers: In clusters of about 5, borne on lateral spurs, petals creamy white with some pink at base, stamens and styles of approximately equal length. Bloom date is approximately April 19, at Yakima, Wash.

Growth control characteristics: Dwarf, compact, at maturity being about one-half the size of a Starkrimson Red Delicious tree on a similar rootstock.

Fruit: Hard ripe; about October 3 or about 150 days from full bloom, at Parker, Wash.

*Size.*—Uniform. Axial diameter — from 3½ inches to 4 inches. Transverse diameter — from 3 inches to 3½ inches.

*Form.*—Slightly irregular; ribbed.

*Longitudinal section* (*see photo* 10).—Round; conic; slightly irregular;

*Transverse section* (*see photo* 11).—Angular; slightly irregular; sides mostly equal.

*Cavity at stem end.*—Symmetrical; acute toward apex. Depth — about ½ inch. Breadth — about ¾ inch. Markings — none. Color — red.

*Basin at calyx end.*—Symmetrical; five crowned ribbed. Depth — ⅜ inch. Breadth — 1 inch. Color — light red.

*Stem.*—Stout. Length — about 1 inch long.

*Calyx.*—Mostly closed; segments persistent.

*Calyx lobes.*—Erect; reflexed; separated at base; about ⅜ inch long. Inner surface — pubescent. Outer surface — glabrous. Eye — small; partially closed. Skin — thick; smooth; glossy; waxed. Dots — obscure; many; small; circular; slightly depressed. Color — white. Distribution — more numerous on capical end than basal end. Ground Color — dark red. Color markings — bright solid red blush over all. Bloom — abundant. Scarfskin — wanting. General color effect — solid, bright-red blush over entire surface of fruit.

*Flesh.*—Juicy. Color — white. Texture — firm; fine; crisp. Flavor — mild; sweet rich. Aroma — fragrant; pronounced. Quality — best; dessert type.

*Core.*—Median. Bundle area (longitudinal section) medium large; conic; symmetrical; alternate with cell. Halves of core area — nearly equal. Bundles — slightly conspicuous. Color — green. Alternate bundles — converge at stamens. Carpels — star-shaped; abaxile; smooth; mucronate; symmetrical. Cross section — ovate. Cell walls — thick; tough. Length — ½ inch. Breadth — ⅜ inch.

*Core cavity.*—Smooth.

*Core lines.*—Clasping.

*Calyx tube.*—Funnel shaped; smooth; long.

*Length of funnel.*—⅜ inch. Width of funnel — ½ inch.

*Styles.*—Distinct; slightly shorter than stamens.

*Stamens.*—Median; one distinct whorl.

*Auxiliary cavity.*—Wanting.

*Sepals.*—Erect; convergent.

*Seeds.*—Usually 2 per carpel; perfect; small; moderately plump. Color — reddish brown. Point of seed — acute. Length — about ¼ inch. Breadth — about ⅛ inch.

Having thus disclosed my invention, I claim:

1. A new and distinct variety of apple tree, substantially as described and shown herein, distinguished principally from other varieties of its type by its compact, dwarf growth habit.

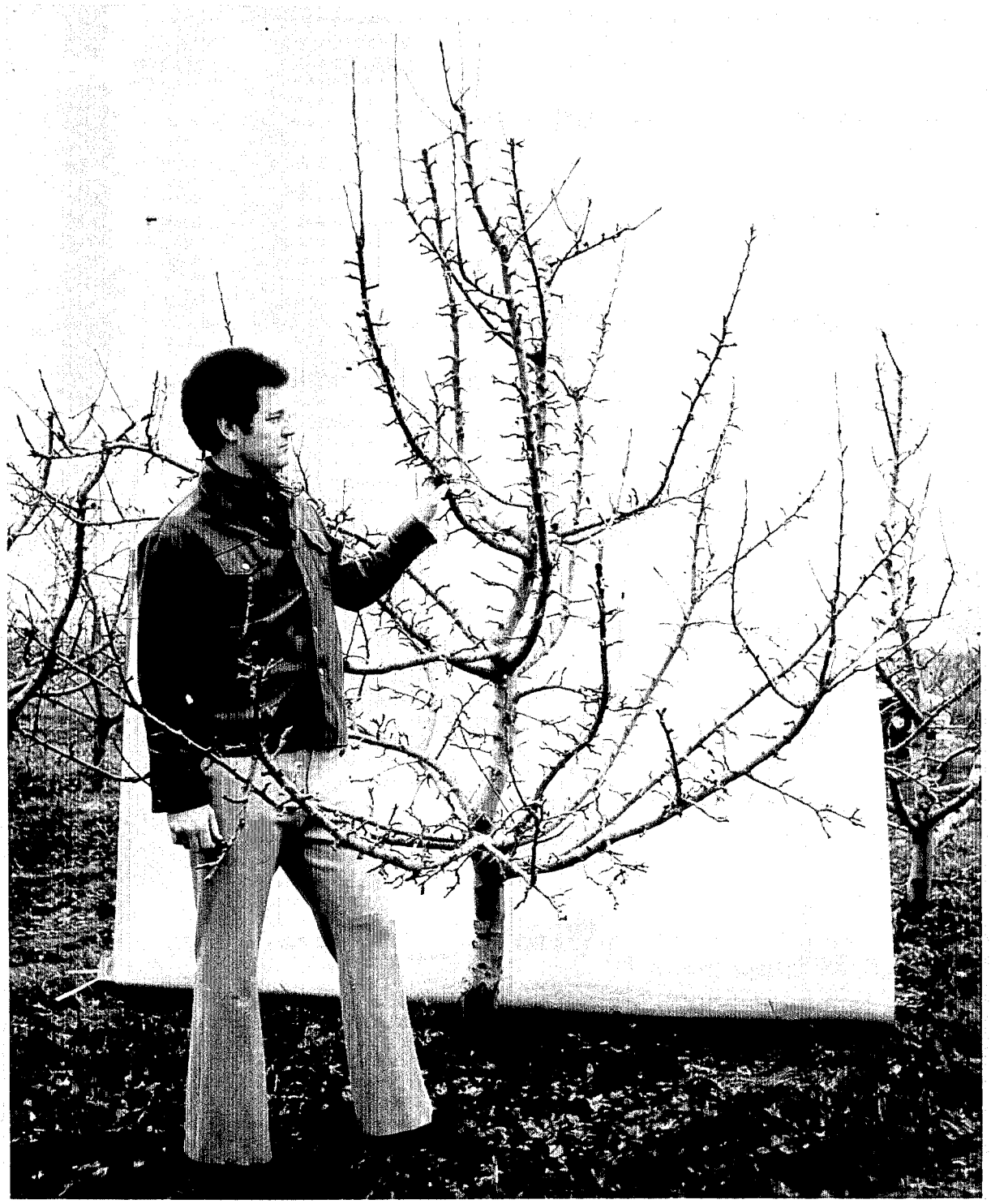

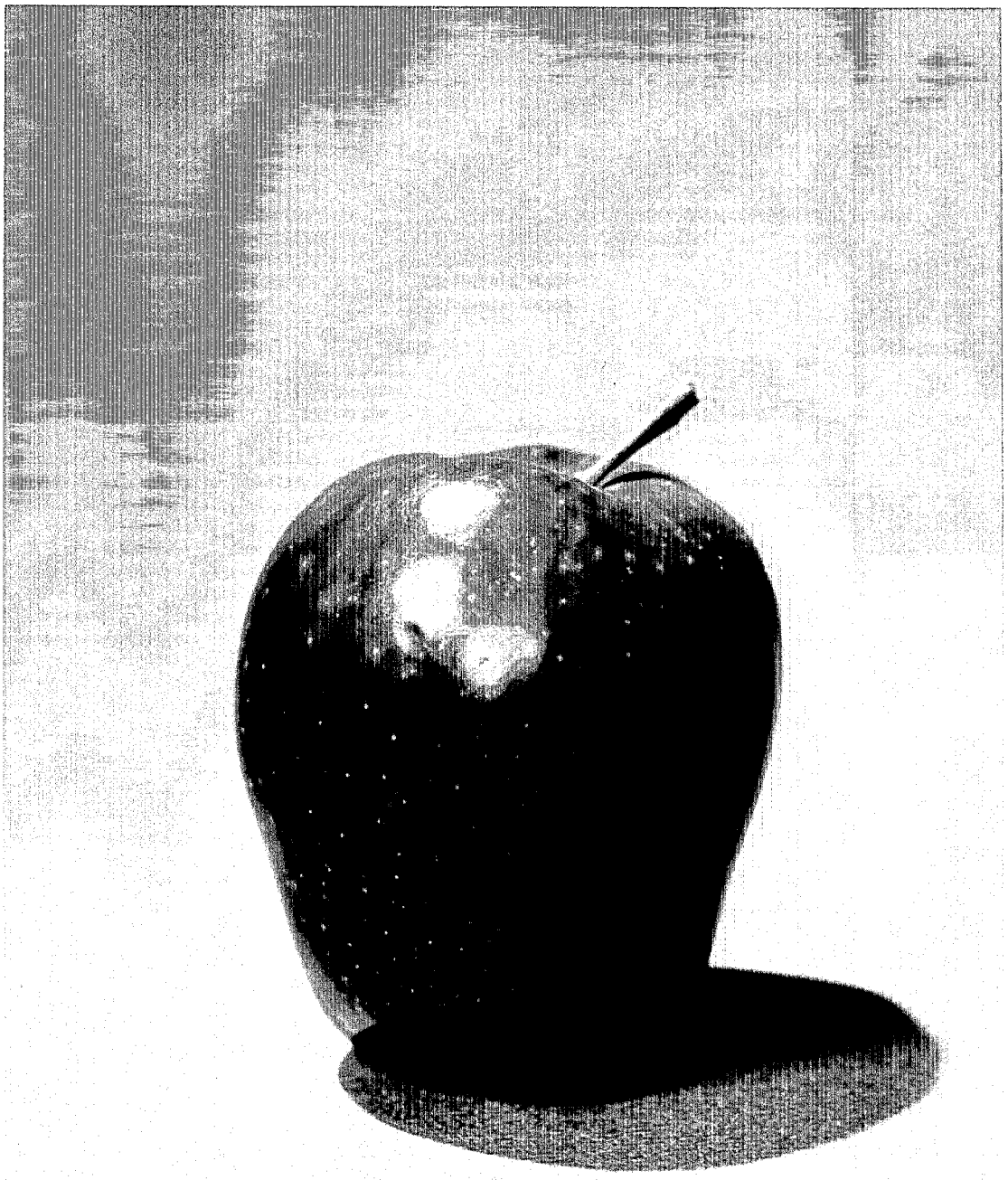

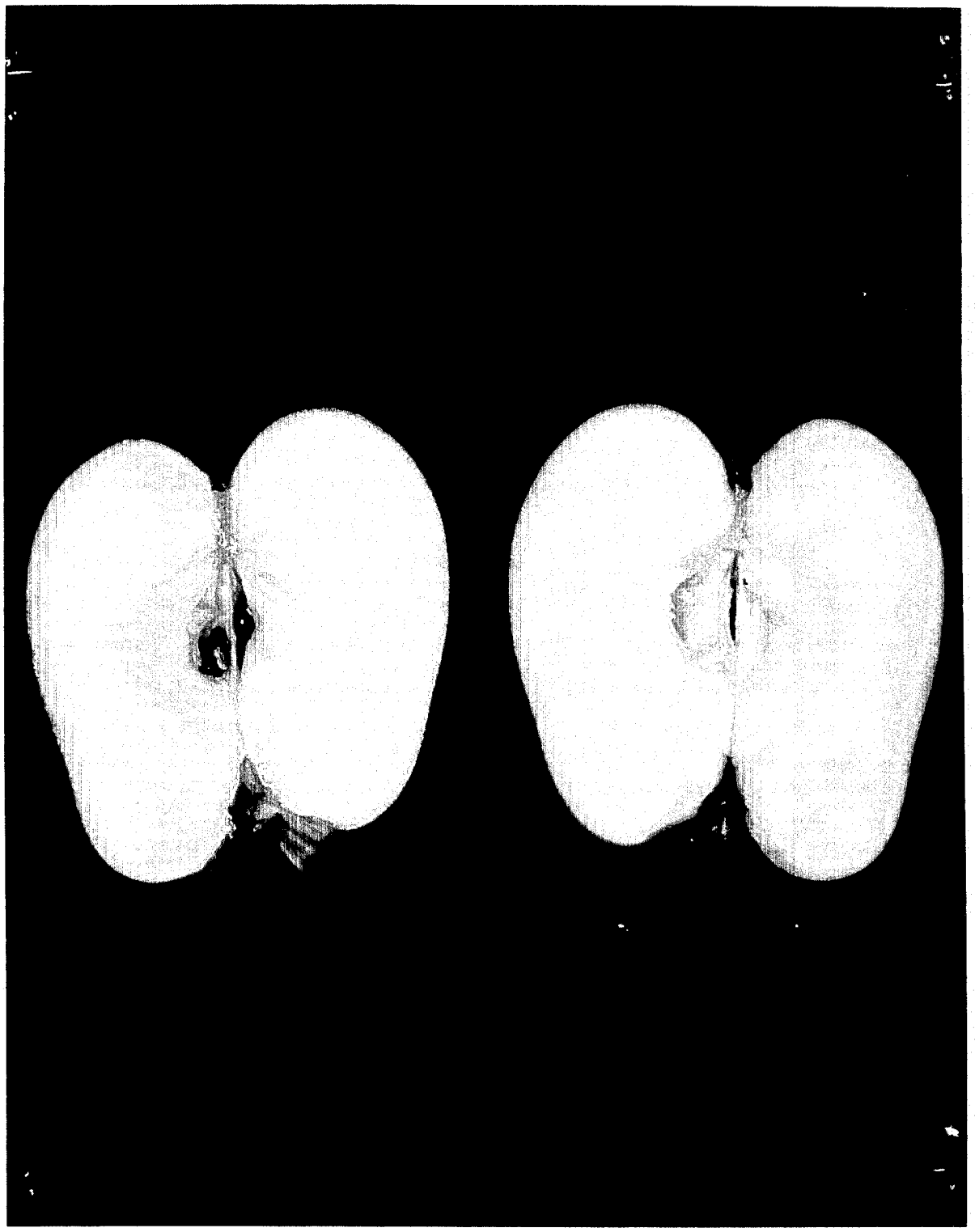

* * * * *